United States Patent [19]

Heiber et al.

[11] Patent Number: 5,346,701
[45] Date of Patent: Sep. 13, 1994

[54] TRANSMUCOSAL DELIVERY OF MACROMOLECULAR DRUGS

[75] Inventors: Sonia J. Heiber; Charles D. Ebert; Sirish C. Dave, all of Salt Lake City, Utah

[73] Assignee: TheraTech, Inc., Salt Lake City, Utah

[21] Appl. No.: 27,508

[22] Filed: Feb. 22, 1993

[51] Int. Cl.$^5$ ............................................. A61F 13/02
[52] U.S. Cl. ................................... 424/435; 424/434; 514/953
[58] Field of Search ................... 424/434, 435; 514/953

[56] References Cited

U.S. PATENT DOCUMENTS

| | | | |
|---|---|---|---|
| 4,772,470 | 9/1988 | Inoue et al. | 424/435 |
| 4,994,439 | 2/1991 | Longenecker et al. | 514/975 |
| 5,204,108 | 4/1993 | Illum | 424/434 |

Primary Examiner—Carlos Azpuru
Attorney, Agent, or Firm—Thrope, North & Western

[57] ABSTRACT

A method and system for mucosally administering a macromolecular drug to mucosa of the oral cavity is shown. The system comprises an inner drug/enhancer/polymer layer having one surface adapted to contact and adhere to the mucosal tissue of the oral cavity and an opposing surface in contact with and adhering to an overlying inert layer. The inner layer contains from about two to sixty percent by weight of a bile salt enhancer, five to sixty five percent by weight of a hydrophilic polymer which is water soluble or swellable and an effective amount of a macromolecular drug having a molecular weight of at least 500 daltons. Polysaccharides, polypeptides and proteins are preferred forms of macromolecular drugs. The bile salt enhancer facilitates the delivery of macromolecules such as low molecular weight heparin and calcitonin. The polymer serves as a plasticizer to prevent the crystallization and/or aggregation of such macromolecular drugs. Hydroxypropyl cellulose is a particularly suitable polymer.

24 Claims, 12 Drawing Sheets

TRANSMUCOSAL DELIVERY OF MACROMOLECULAR DRUGS

BACKGROUND OF THE INVENTION

This invention relates to a dosage form and a method for delivering macromolecular drugs to a human or animal. More particularly, this invention relates to a dosage form and a method for delivering charged or uncharged macromolecular drugs to a warm-blooded animal by transmucosal administration and particularly to the buccal and sublingual tissues of the oral cavity.

The delivery of macromolecular drugs presents one of the greatest challenges in pharmaceutical science. Recently there has been much interest in the use of membranes of the oral cavity as sites of drug administration. Both the buccal and sublingual membranes offer advantages over other routes of administration. For example, drugs administered through the buccal and sublingual routes have a rapid onset of action, reach high levels in the blood, avoid the first-pass effect of hepatic metabolism, and avoid exposure of the drug to fluids of the gastrointestinal tract. Additional advantages include easy access to the membrane sites so that the drug can be applied, localized, and removed easily. Further, there is good potential for prolonged delivery through the buccal membrane. M. Rathbone & J. Hadgraft, 74 *Int'l J. of Pharmaceutics* 9 (1991). Administration through the buccal mucosa may be better accepted than rectal dosing, for example, and generally avoids local toxic effects, such as has been a problem in nasal administration. B. Aungst & N. Rogers, 53 *Int'l J. Pharmaceutics* 227, 228 (1989).

The sublingual route has received far more attention than has the buccal route. The sublingual mucosa includes the membrane of the ventral surface of the tongue and the floor of the mouth whereas the buccal mucosa constitutes the lining of the cheek. The sublingual mucosa is relatively permeable, thus giving rapid absorption and acceptable bioavailabilies of many drugs. Further, the sublingual mucosa is convenient, accessible, and generally well accepted. This route has been investigated clinically for the delivery of a substantial number of drugs. It is the preferred route for administration of nitroglycerin and is also used for buprenorphine and nifedipine. D. Harris & J. Robinson, 81 *J. Pharmaceutical Sci.* 1 (1992).

The buccal mucosa is less permeable than the sublingual mucosa. The rapid absorption and high bioavailabilies seen with sublingual administration of drugs is not generally provided to the same extent by the buccal mucosa. D. Harris & J. Robinson, 81 *J. Pharmaceutical Sci.* (1992) at 2. The permeability of the oral mucosae is probably related to the physical characteristics of the tissues. The sublingual mucosa is thinner than the buccal mucosa, thus permeability is greater for the sublingual tissue. The palatal mucosa is intermediate in thickness, but is keratinized whereas the other two tissues are not, thus lessening its permeability.

The ability of molecules to permeate through the oral mucosa appears to be related to molecular size, lipid solubility, and ionization. Small molecules, less than about 100 daltons, appear to cross the mucosa rapidly. As molecular size increases, however, permeability decreases rapidly. Lipid-soluble compounds are more permeable through the mucosa than are non-lipid-soluble molecules. In this regard, the relative permeabilities of molecules seems to be related to their partition coefficients. The degree of ionization of molecules, which is dependent on the $pK_a$ of the molecule and the pH at the membrane surface, also greatly affects permeability of the molecules. Maximum absorption occurs when molecules are unionized or neutral in electrical charge; absorption decreases as the degree of ionization increases. Therefore, charged macromolecular drugs present the biggest challenge to absorption through the oral mucosae.

Substances that facilitate the transport of solutes across biological membranes, penetration enhancers, are well known in the art for administering drugs. V. Lee et al., 8 *Critical Reviews in Therapeutic Drug Carrier Systems* 91 (1991) [hereinafter "*Critical Reviews*"]. Penetration enhancers may be categorized as chelators (e.g., EDTA, citric acid, salicylates), surfactants (e.g., sodium dodecyl sulfate (SDS)), non-surfactants (e.g., unsaturated cyclic ureas), bile salts (e.g., sodium deoxycholate, sodium tauro-cholate), and fatty acids (e.g., oleic acid, acylcarnitines, mono- and diglycerides). The efficacy of enhancers in transporting both peptide and nonpeptide drugs across membranes seems to be positively correlated with the enhancer's hydrophobicity. *Critical Reviews* at 112. For example, the efficacy of bile salts in enhancing the absorption of insulin through nasal membranes was positively correlated with the hydrophobicity of the bile salts' steroid structure. *Critical Reviews* at 115. Thus, the order of effectiveness was deoxycholate < chenodeoxycholate < cholate < ursodeoxycholate. Conjugation of deoxycholate and cholate, but not fusidic acid derivatives, with glycine and taurine did not affect their enhancement potency. Transmucosal intestinal delivery of heparin was not apparent in terms of showing prolongation of partial thromboplastin time or release of plasma lipase activity when administered through the colon of a baboon. However, significant activity was detected when the bile salts, sodium cholate or deoxycholate, were included in the formulation. *Critical Reviews* at 108.

Various mechanisms of action of penetration enhancers have been proposed. These mechanisms of action, at least for peptide and protein drugs, include (1) reducing the viscosity and/or elasticity of mucus layer, (2) facilitating transcellular transport by increasing the fluidity of the lipid bilayer of membranes, (3) facilitating paracellular transport by altering tight junctions across the epithelial cell layer, (4) overcoming enzymatic barriers, and (5) increasing the thermodynamic activity of the drugs. *Critical Reviews* at 117–125.

Many penetration enhancers have been tested and found effective in facilitating mucosal drug administration. Moreover, hardly any penetration enhanced products have reached the market place. Reasons for this include lack of a satisfactory safety profile respecting irritation, lowering of the barrier function, and impairment of the mucociliary clearance protective mechanism. *Critical Reviews* at 169–70. Another factor that must be dealt with for any enhancer that is to be administered through the buccal or sublingual membranes is the unpleasant taste associated with essentially all of the known enhancers. Further, in order for an enhancer to function adequately, the enhancer and drug combination is preferably held in position against mucosal tissues for a period of time sufficient to allow enhancer assisted penetration of the drug across the mucosal membrane. In transdermal technology, this is often accomplished by means of a patch or other device which adheres to the skin layer by means of an adhesive. In many instances, such as is the case in many macromolecules, the drug may crystallize or not be sufficiently soluble in the enhancer. Thus, a solvent or some other means may be required to provide the degree of drug/enhancer compatibility required to form a functioning system. The isolating of a macromolecular drug/enhancer combination to provide exposure to a designated mucosal area coupled with maintaining the drug in a physical form suitable for passage through the mucosal tissues presents unique problems which need to be overcome for an effective delivery system, particularly through mucus in the oral cavity. This problem is further exacerbated when the drug and/or the enhancer of choice are distasteful in flavor.

Oral adhesives are well known in the art. See, for example, Tsuk et al., U.S. Pat. Nos. 3,972,995; Lowey, 4,259,314; Lowey, 4,680,323; Yukimatsu et al., 4,740,365; Kwiatek et al., 4,573,996; Suzuki et al., 4,292,299; Suzuki et al., 4,715,369; Mizobuchi et al., 4,876,092; Fankhauser et al., 4,855,142; Nagai et al., 4,250,163; Nagai et al., 4,226,848; Browning, 4,948,580; Schiraldi et al., U.S. Pat. No. Re. 33,093; and J. Robinson, 18 Proc. Intern. Symp. Control. Rel. Bioact. Mater. 75 (1991). Typically, these adhesives consist of a matrix of a hydrophilic, e.g., water soluble or swellable, polymer or mixture of polymers which can adhere to a wet mucous surface. These adhesives may be formulated as ointments, thin films, tablets, troches, and other forms. Often, these adhesives have had medicaments mixed therewith to effectuate slow release or local delivery of a drug. Some, however, have been formulated to permit adsorption through the mucosa into the circulatory system of the individual.

There is nothing in the art which is directed specifically with overcoming problems associated with enhancer assisted buccal or sublingual delivery of large drug molecules wherein the drug molecule is subject to crystallization and at least one member of the combination is of objectionable flavor.

As an example, heparin, a drug having potent anticoagulation properties, is a polyanionic molecule having marginal flavor. Native heparin exists mainly in the lungs, intestine, and liver of a variety of mammals. It is also found in high levels intracellularly in mucosal mast cells, connective tissue mast cells and basophilic leukocytes. Commercial heparin preparations are mostly obtained from porcine intestinal mucosa or beef-lung. It is composed of alternating 1–4-linked uronic acid and D-glucosamine residues. The uronic acid residues are either L-iduronic acid or D-glucuronic acid; D-Glucosamine residues are either N-sulfated (major proportion) or N-acetylated (minor proportion). Thus, heparin is a polyanion exhibiting a strong negative charge at neutral pH. Heparin is extremely heterogeneous in both structure and molecular weight because the biosynthesis of the native precursors, heparin-proteoglycans (M. W. 750,000 to 1,000,000), are usually not completed. Low molecular weight heparin (LMWH) refers to the fractionated or depolymerized heparin, which has a lower molecular weight than the normal commercial grade heparin, i.e. between about 4000–6000 daltons.

The anticoagulant properties of heparin have been demonstrated to be associated with binding to antithrombin III (AT III). At III is a plasma glycoprotein with molecular weight of approximately 58,000. AT III binds with thrombin very tightly in a 1:1 stoichiometric ratio, which blocks the active site on thrombin and prevents it from interacting with fibrinogen. However, the inhibition rate of thrombin with AT III is low in the absence of heparin. Heparin dramatically accelerates the rate of thrombin inactivation up to 2000-fold. Clinically used heparin can be separated into two distinct fractions according to its affinity for AT III. Approximately 33% of heparin has a high affinity for AT III, which has potent anticoagulant activity (up to 90% of the activity of the unfractionated heparin). A low-affinity heparin binds to the same site on AT III, but with approximately 1000 times lower affinity.

Although anticoagulation is its major pharmacological activity, heparin has many other functions. Heparin inhibits the proliferation of vascular smooth muscle cells and renal mesengial cells, suppresses the delayed-type hypersensitivity, and inhibits angiogenesis. Other pharmacological functions of heparin include anti-thrombotic effect, antibacterial, antivirus, and antitumor angiogenesis, particularly in combination with cortisone. Although it has been clinically observed that heparin may induce thrombocytopenia, in vitro studies have shown that normal heparin enhances the release of platelets. Moreover, various heparin-binding growth factors can be purified with heparin affinity chromatography.

Heparin has been extensively used in many clinical applications, including cardiac surgery, peripheral vascular surgery, dialysis, autotransfusion, transplantation, the treatment of pulmonary embolism, disseminated intravascular coagulation, and venous thrombosis. The dosage is dependent on the type of application. Heparin has also been used as a prophylactic agent against deep vein thrombosis. The dose of heparin for this treatment is relatively low, e.g., 10,000 U/24 hr for subcutaneous administration. Heparin is also of value in the treatment of thromboembolic disorders, such as pulmonary embolism and arterial thrombosis. These treatments require relatively high doses of heparin, approximately 30,000 U/24 hr.

The transmucosal administration of heparin, particularly via the oral cavity by buccal or sublingual delivery, has been heretofore unavailable. However, as referenced above, there is a need for a practical means for the delivery of heparin or other macromolecules, particularly those in ionic form, by means of buccal or sublingual administration.

OBJECTS AND SUMMARY OF THE INVENTION

It is an object of the present invention to provide a dosage form and method for administering macromolecular drugs to humans and animals through the buccal and sublingual routes.

It is also an object of the invention to provide a dosage form and method for administering charged and uncharged macromolecular drugs to humans and animals that allows easy accessibility to the site of administration.

It is another object of the invention to provide a dosage form and method for administering charged and uncharged macromolecular drugs to humans and animals that promotes high patient acceptance and compliance.

It is a further object of the invention to provide a dosage form and method for administering charged and uncharged macromolecular drugs to humans and animals that allows for localization of dosage forms over a prolonged period to maximize drug absorption.

It is still another object of the invention to provide a dosage form and method for administering charged and uncharged macromolecular drugs to humans and animals that provides acceptable tissue compatibility of the dosage form.

It is yet another object of the invention to provide a dosage form and method for administering charged and uncharged macromolecular drugs to humans and animals through the buccal and sublingual mucosae that avoids the bad taste associated with penetration enhancers.

These and other objects may be accomplished by means of a macromolecular drug/enhancer/polymer formulation comprising a macromolecular drug having a molecular weight in excess of 500 and preferably in excess of about 1000 admixed with a bile salt or bile salt analog enhancer and intimately admixed with a hydrophilic polymer, i.e. a polymer which is either water swellable or soluble, and which serves as a plasticizer for the macromolecular drug and as a position retainer for the drug/enhancer combination against the mucosal tissues. Such a formulation is formulated as a bilayer system wherein the drug/enhancer/polymer combination forms a layer adapted to contact and adhere to the sublingual or buccal mucosa. Overlaying the drug/enhancer/polymer is an outer or cover layer which is substantially impermeable to bile salt enhancer or drug. Macromolecules, such as heparin, and bile salt enhancers have objectionable flavors and the outer layer is designed to reduce or prevent the flow of these components out of the lower layer into the oral cavity by means of saliva or other fluids in the mouth, e.g. by water or other liquids being ingested. This bilayer system can be either in the form of a tablet or a patch. In a tablet the outer layer is an inert, nonadhesive material which facilitates insertion of the tablet by the patient and prevents incidental adhesion of other oral tissue, such as the tongue, to the tablet. In a patch, the outer layer is a film or membrane and is preferably a permselective membrane having a molecular weight cutoff which prevents the outflow of macromolecular drug or bile salt but allows the inflow of water or other smaller molecules into the lower layer. This membrane layer can be either insoluble or of a selected solubility to dissolve after the delivery of the drug and enhancer. This membrane performs the same function as the outer layer of the tablet except that it allows the influx of water and other desired agents or ingredients into the drug/enhancer/adhesive layer. The invention is particularly directed to macromolecular drugs selected from the group consisting of polysaccharides, peptides and proteins having molecular weights of between about 500 and 10,000 or even higher if functional. Exemplary of these are heparin as a polysaccharide and calcitonin as a polypeptide.

BRIEF DESCRIPTION OF THE DRAWINGS

FIG. 1 shows a bilayer tablet embodiment and FIG. 2 shows a filmpatch embodiment having an optional adhesive overlay.

DETAILED DESCRIPTION OF THE INVENTION

Figure 1:
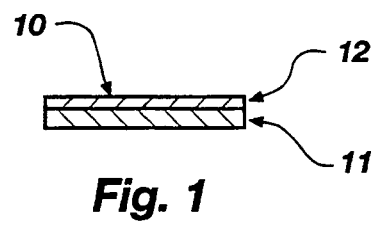
FIGS. 1 and 2 are schematic diagrams of buccal systems or devices suitable for use in the present invention.

For the purposes of this disclosure the following definitions will apply:

A "macromolecular drug" is a drug having a molecular weight above 500 daltons (preferably above 1000), and is preferably a polysaccharide, peptide or protein. Molecules having molecular weights between about 500 and 10,000 are preferred and molecules within that range which are ionize or charged are particularly preferred. However, macromolecules having molecular weights in excess of 10,000 are not to be precluded as the only limitation to the molecular weight is that of functionality.

"Low molecular weight heparin" or "LMWH" is heparin having a molecular weight in the range of 4000 to 6000.

"Bile salt" refers to the steroidal detergents which are the natural or synthetic salts of cholanic acid, e.g. the salts of cholic and desoxycholic acid or combinations of such salts. The salts of the conjugates of the bile acid with glycine or taurine are preferred with the taurine salts being particularly preferred. Bile salt analogs having the same physical characteristics which also function as penetration enhancers are also included in this definition.

"NaTC" is the bile salt, sodium taurocholate.

"CHAPS" is the bile salt analog, 3-[(3-cholamidopropyl)dimethylammonio]-1-propane sulfate, inner salt.

"IU" refers to anti-factor $X_a$ units as assayed against the First International Low Molecular Weight Heparin standard.

"Polymer", "adhesive polymer", "mucoadhesive", or such similar terms refers to hydrophilic polymers, natural or synthetic, which, by the hydrophilic designation, can be either water soluble or swellable and which are compatible with the bile salt enhancers and macromolecular drugs. Preferably such polymers have a dual function serving as adhesives for adhering the drug/enhancer/polymer formulation to the mucous tissues as well as functioning as plasticizers for the macromolecular drugs, retaining the drugs in solution or suspension and preventing the self association (aggregation) and/or crystallization thereof. This is particularly true in formulations which require high drug loading with crystalline drugs. In these instances the polymer can act as a plasticizer affording formulation integrity and stability. These polymers are also selected to promote desired drug release profiles and do not adversely affect the activity of the drug. Such polymers are inclusive of hydroxypropyl cellulose, hydroxypropyl methylcellulose, hydroxy ethylcellulose, ethylcellulose, carboxymethyl cellulose, dextran, gaur-gum, polyvinyl pyrrolidone, pectins, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, and the like.

The delivery system of the present invention comprises an inert outer or backing layer or membrane and an inner drug/enhancer/polymer layer. In the inner layer, the concentration of the drug may vary according to its potency and bioavailability. Hence, the concentration of the drug will be an "effective amount" which is the amount required to achieve the desired delivery across mucosal tissues at a rate and for a time which will achieve the desired physiological effect. Those concentrations can be readily determined by the practitioner based upon the drug selected. Generally, these amounts may vary between about 0.01 and 88 percent by weight. The bile salt enhancer may generally be present in amounts between about 2 to 60 percent by weight with ranges between about 4 to 50 percent by weight being preferable. The polymer may be present in ranges as needed to contain the drug/enhancer and provide the desired plasticizing effect for the drug. Generally ranges between about 5 to 65 percent by weight may be used with ranges between about 10 to 55 percent by weight being preferable. If additional agents or ingredients are utilized, the remainder of the formulation may be made up of inert ingredients or formulation aids such as lactose, magnesium stearate, flavoring agents coloring agents, stabilizers, or any other fillers, binding agents and the like which do not have a negative impact on the functioning of the drug/enhancer/polymer combination. These may generally vary from 0 up to about 60 percent by weight of the inner layer formulation.

As an indication of the variances in drug concentration which may provide "effective amounts", when using the polysaccharide LMWH as the drug, the concentration range may vary from about 25 to 75 percent by weight of the drug/enhancer/polymer combination but, when using the polypeptide calcitonin as the drug, the concentration may vary from about 0.05 to 2.5 percent by weight. Thus, it is readily apparent that the drug concentration will of necessity be determined by the drug being utilized and its potency and/or bioavailability.

Figure 2:
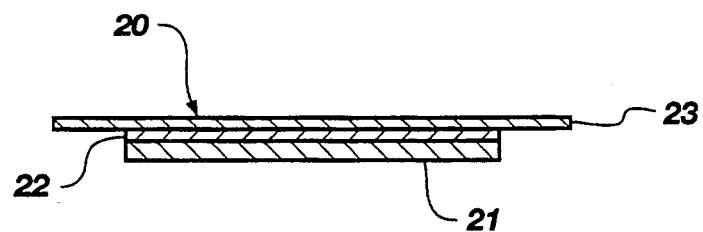

As previously stated, the systems utilized in the present invention comprise an inner or underlying layer containing the drug/enhancer/polymer and an overlying inert layer. As shown in FIGS. 1 and 2 the systems may be in either the form of a tablet or a patch. Both patches and tablets are prepared such that one layer is contains the drug/enhancer/polymer, and is preferably adhesive while the other layer is inert and non-adhesive, at least on the outer surface. FIG. 1 shows a bilayer tablet 10 having an underlying layer 11 containing the drug/enhancer/polymer combination and an outer inert layer 12. FIG. 2 shows a filmpatch embodiment wherein the patch 20 consists of an underlying drug/enhancer/polymer layer 21 and an outer inert membrane layer 22 having the same diameter as active layer 21. However, the outer inert layer of a patch may extend beyond the outer periphery of the underlying active layer and have contained on the under surface thereof, additional mucoadhesive (not shown) or, as shown in FIG. 2, there may be an optional overlay 23 containing a mucoadhesive on the inner surface of overlay 23 which extends beyond the outer periphery of both the active layer 21 and the inert membrane layer 22. In this manner, the active or inner layer is completely surrounded by the overlying membrane which adheres to the mucosa and further insures that the drug/enhancer combination will remain in the area of the oral mucosa in which it is applied until the drug/enhancer portions of the layer have been adequately delivered. The optional overlay 23 may also be a perm-selective membrane having a desired molecular cutoff pore structure. In certain instances it may be beneficial to have both membrane 22 and overlay 23 both be MWCO membranes, each having a different MWCO value for controlling or varying the amount or degree of water or other materials passing through such membranes.

Bilayer tablets are made by classical bilayer tablet compression techniques on a suitable press. In reference to FIG. 1, the bilayer tablets 10 consist of an active layer 11 and an inert layer 12 which may be of a different color to distinguish the layers for purposes of application. The identification of the inert non-adhesive layer 12 facilitates application by the patient and prevents incidental adhesion of other oral tissues to the tablet. The inner layer 11 is prepared by dry mixing the ingredients and compressing them into a tablet or by wet granulating the ingredient mixture and then compressing according to accepted pharmaceutical techniques. In general, it has been found suitable to mix the drug, bile salt enhancer, polymer and any formulation aids such as magnesium stearate, lactose, flavors, and the like and then compress the mix in a press at about 0.2–0.5 tons for a dwell time of 2–10 seconds.

The inert layer 12 is first prepared by intimately admixing a non-adhesive polymer such as ethyl cellulose and a tableting excipient such as sorbitol with any other formulation aids such as dyes, flavors, magnesium stearate and the like. This may be formulated as a dry mix or accomplished by conventional wet granulation and screening techniques followed by drying. In either event, the blended inert layer ingredients are then placed on top of the partially compressed inner layer and both layers are then compressed at a higher pressure, for example from 0.5 to 1.5 tons for an additional 2–10 seconds dwell time.

When formulating patches using permselective or other membranes, a mixture of drug/enhancer/polymer, as a solution or viscous mixture, may be cast onto a suitable membrane. A mold may be used to control the area of the active layer if desired. In the alternative, a solution of suitable membrane polymer may be sprayed or otherwise coated onto the drug/enhancer/polymer.

With reference to FIG. 2, the filmpatches 20 are to be applied to the oral mucosa with the active side or layer 21 against the mucosa and the membrane 22 (and optional overlying membrane 23) facing the oral cavity. During the course of the enhancer assisted drug permeation, water can readily permeate through the pores of the perm-selective membrane 22 (and optional membrane 23) while the inner macromolecular drug/enhancer/polymer layer 21 remains restricted to the patch site. This has the effect of limiting the taste of patch ingredients and controlling water permeation rates to keep the hydration of the polymer and local concentrations of drug/enhancer/polymer relatively high levels thereby increasing the transmucosal flux. The active layer 21 will generally dissolve within a relatively short time period, e.g. 10 to 60 minutes, and the perm-selective membranes 22 and 23 can then be removed. Alternatively, the membranes 22 and 23 can be formulated to dissolve over a selected period of time.

In the case of heparin patch formulation, an aqueous solution of the bile salt enhancer is added to a concentrated aqueous solution of heparin and stirred until clear. An alcoholic or hydro-alcoholic solution of polymer is then added and the resulting viscous mixture is cast onto a dry perm-selective membrane. The dried mixture is homogeneous and translucent and can be punched into a disk or other proper form. A slurry method may also be used wherein the bile salt enhancer, the LMWH and the polymer can be added to an ethanol solution to form a slurry which can then be cast onto a membrane. Alternative methods, not using alcohol, may be used when formulating polypeptides and proteins to avoid denaturization.

The polymers which are useful as perm-selective layers in these formulations are chosen to promote desired release profiles of the macromolecular drug being administered. For example, they may be chosen because they do not bind the drug if rapid release is necessary or they can be chosen to prolong release if binding is desired. In either event, they do not deleteriously influence drug activity. In the preferred case, the perm-selective membrane is permeable to small molecules such as water but not to the macromolecular drugs, enhancers, polymers, adjuvants and the like. A preferred membrane is a MWCO (molecular weight cutoff) dialysis membrane made of cellulose or cellulose acetate wherein the molecular weight cutoff is selected according to the weight of the drug, enhancer, etc. For example, MWCO dialysis membranes having a cutoff of about 100–500 are deemed to be suitable in most instances. Other materials, such as reverse osmosis membranes, film forming polymers, crosslinked polymers such as silicones, polyurethanes and rubbers, gels including hydrogels, and various starches are also suitable.

The systems of the present invention will preferably be sized to provide between about 0.5 to 10 $cm^2$ of surface area for contact between the active or inner layer and the mucosa. Areas of between about 0.5 to 5 $cm^2$ are preferred with areas of between about 1.0 and 5 $cm^2$ being optimal. The inner or active layer will generally have a thickness of between about 0.1 and 3 mm with thicknesses of between about 0.5 and 2 mm being preferred.

The following examples are illustrative of methods of preparing both bilayer tablets and film patches.

EXAMPLE 1

LMWH tablets are prepared in the following manner. An active LMWH layer was prepared by dry blending 2.010 g LMWH, 0.504 g of hydroxypropyl cellulose, (KLUCEL LF) and 0.450 g of NaTC. To this was added 500 µl of 200 proof ethanol and the mixture was wet blended to give a wet granulation having a dough like consistency. The wet granulation was passed through an 18 mesh screen and allowed to dry for 3 hours in a draft oven at 25° C. The dried granulation was then passed through a 20 mesh screen and placed in a glass vial with 0.030 g of magnesium stearate and 0.006 g of mint flavor and dry blended again. A 100 mg amount of this mixture was filled into a ½" diameter die and precompressed on a Carver Press Model C with 0.25 ton pressure for a 3 second time dwell time to form the active drug/enhancer/polymer layer.

An inert layer was prepared by dry blending 2.0 g of ethyl cellulose (Ethocel), 5.81 g of sorbitol and 0.0048 g of Colorcon FD&C Yellow #6 HT Aluminum Lake dye. To this was added 700 µl of 200 proof ethanol and the mixture was wet blended to provide a wet granulation having a dough like consistency. The wet granulation was passed through an 18 mesh screen and allowed to dry for 3 hours in a draft oven at 25° C. The dried granulation was then passed through a 20 mesh screen and placed in a glass vial with 0.16 g of magnesium stearate and 0.024 g. of mint flavor and dry blended again. A 100 mg sample of this material was placed on top of the partially compressed active layer and both layers were then compressed at 1 ton pressure for a 3 second dwell time to yield a bilayer tablet suitable for buccal delivery.

This provides a bilayer tablet disk having a surface area diameter of ½" wherein the active layer contains 200 mg LMWH (67% by weight), 45 mg. NaTC (15% by weight) 50.4 mg hydroxypropyl cellulose (16.8% by weight) and 1.2% by weight formulation aids or flavoring agents.

EXAMPLE 2

The procedure of Example 1 was followed with the following modifications. The bile salt analog, CHAPS, was used as the enhancer in the place of NaTC and the amounts of the components of the active layer were varied to provide an active layer containing 200 mg LMWH (67% by weight), 15 mg. CHAPS (5% by weight) 80.4 mg hydroxypropyl cellulose (26.8% by weight) and 1.2% by weight formulation aids or flavoring agents.

EXAMPLE 3

The procedure of Example 1 was followed with the exception that the amounts of the components of the active layer were varied to provide an active layer containing 100 mg LMWH (33.5% by weight), 45 mg. NaTC (15% by weight) 150.9 mg hydroxypropyl cellulose (50.3% by weight) and 1.2% by weight formulation aids or flavoring agents.

EXAMPLE 4

The procedure of Example 1 was followed to prepare a buccal tablet wherein the lower or active layer contained 1 mg calcitonin (0.25% by weight), 135.2 mg hydroxypropyl cellulose (33.8% by weight), 60 mg NaTC (15% by weight), 199 mg lactose (49% by weight), 4 mg magnesium stearate (1.0% by weight), and 0.8 mg mint flavor (0.2% by weight).

EXAMPLE 5

The procedure of Example 4 was followed to prepare a buccal tablet wherein the lower layer or active contained the same content but was prepared by dry blending and not by wet granulation.

EXAMPLE 6

A buccal patch formulation was prepared containing 200 mg of LMWH using a 500 MWCO dialysis membrane as the outer covering or layer. To a vial was added 268.1 $\mu$l of a 31.14% by weight NaTC aqueous solution and 601.8 $\mu$l of 60.26% by weight LMWH aqueous solution. The solutions were stirred together until a clear solution formed. To this was added and an ethanol solution containing 565.3 $\mu$l of 19.85%, w hydroxypropyl cellulose (Klucel LF) with stirring until an homogeneous mixture was obtained. A 717.63 $\mu$l portion of this mixture was then cast onto a 500 MWCO dialysis membrane, which had been dried in an oven at 70° C. to provide a dry substrate, in a glass mold and allowed to dry overnight. Excess membrane was trimmed from around the translucent homogeneous active layer to yield a finished buccal patch having a surface area of 5 cm$^2$.

The inner or active layer of this patch contained 200 mg LMWH (67.7% by weight), 45 mg NaTC (15.2% by weight) and 50.4 mg hydroxypropyl cellulose (17.1% by weight).

EXAMPLE 7

A 100 mg LMWH patch was prepared using the procedure of Example 6 which contained 100 mg LMWH, 45 mg NaTC and 50 mg hydroxypropyl cellulose (Klucel LF). As in Example 4, the mixture dried to a homogeneous translucent film.

EXAMPLE 8

The procedure of Example 4 was again followed to yield a buccal patch wherein the active layer contained 46 mg LMWH, 21 mg NaTC and 23 mg hydroxypropyl cellulose (Klucel LF).

EXAMPLE 9

A slurry method was used to form a 200 mg LMWH buccal patch. A 45 mg amount of bile salt enhancer (NaTC) and 200 mg of micronized LMWH were added to 278 $\mu$l of 19.85 percent by weight hydroxypropyl cellulose (Klucel LF) in ethanol solution in a vial and stirred until a homogeneous slurry is obtained. This slurry is cast onto a dry 500 MWCO membrane fixed in a glass mold. The mixture dries to an opaque layer, adhering to the membrane.

Transmucosal transport of LMWH was demonstrated using the dog buccal mucosa model. The dog was selected as the animal model because the structure of dog buccal tissue is histologically similar to that of human tissue. C. Ebert et al., Transbuccal absorption of diclofenac sodium in a dog animal model, in Controlled-Release Technology 310-21 (P. Lee, W. Good, eds., ACS Symposium Series, No. 348, American Chemical Society, Washington, D.C., 1987). Rodents tend to have keratinized buccal tissue while dogs, like humans, show well vascularized buccal tissue with no keratinized layer.

Two dosage forms, a bilayer tablet and a filmpatch with an semipermeable backing membrane were used to demonstrate transmucosal transport of LMWH in dogs.

Dosage forms were tested in in vivo experiments to determine their effectiveness in delivering LMWH systemically to dogs. Mongrel dogs (designated as Dogs 1, 2, 4, 6, 7, 9 and 10) each weighing 30-35 kg were conditioned for one month prior to use. The dogs were sedated with Bietal, then anesthetized with Halothane for the duration of each experiment. The saphous vein was catheterized to permit venous blood sampling. Blood samples were collected into citrate "VACUTAINER" tubes and immediately centrifuged for 10 minutes at 3400 rpm. The resultant supernatant plasma was then collected and stored in capped polypropylene tubes at −20° C. until analyzed for coagulation status. All dogs were rested two weeks between tests to minimize the effects of repetitive anesthesia and blood collection.

Anti-Factor X$_a$ Assay

The coagulation status of serum samples was assessed through an anti-factor X$_a$ assay, which is a standard test for determining heparin activity or concentrations. The assay used was the Coatest Heparin Assay Kit obtained from Chromogenix and distributed by Kabi Pharmacia Hepar, Inc. The instructions provided with the assay kit were followed and heparin activity was determined by following such instructions.

Buccal drug permeability from solutions and buccal devices were characterized by a two-step process. First, the disposition kinetics of the drug after bolus intravenous administration was defined for each dog. Second, plasma concentration time profiles after buccal administration were deconvoluted using the pharmacokinetic parameters estimated from the intravenous data (for the same dog) to estimate the drug absorption profile.

Plasma concentration time profiles after intravenous bolus dosing were analyzed in terms of a two-compartment open model with first order elimination. The biexponential rate equation associated with this model was fitted to the experimental data using a nonlinear least squares procedure. The absorption profile (amount of LMWH absorbed as a function of time) was estimated by the Loo-Reiegelman method, J. Loo & Riegelman, 57 J. Pharmaceutical Sci. 918-28 (1968), using the macroscopic rate constants calculated from the intravenous data for the same dog.

Drug Dosage Kinetics after Intravenous Administration

Figure 3:
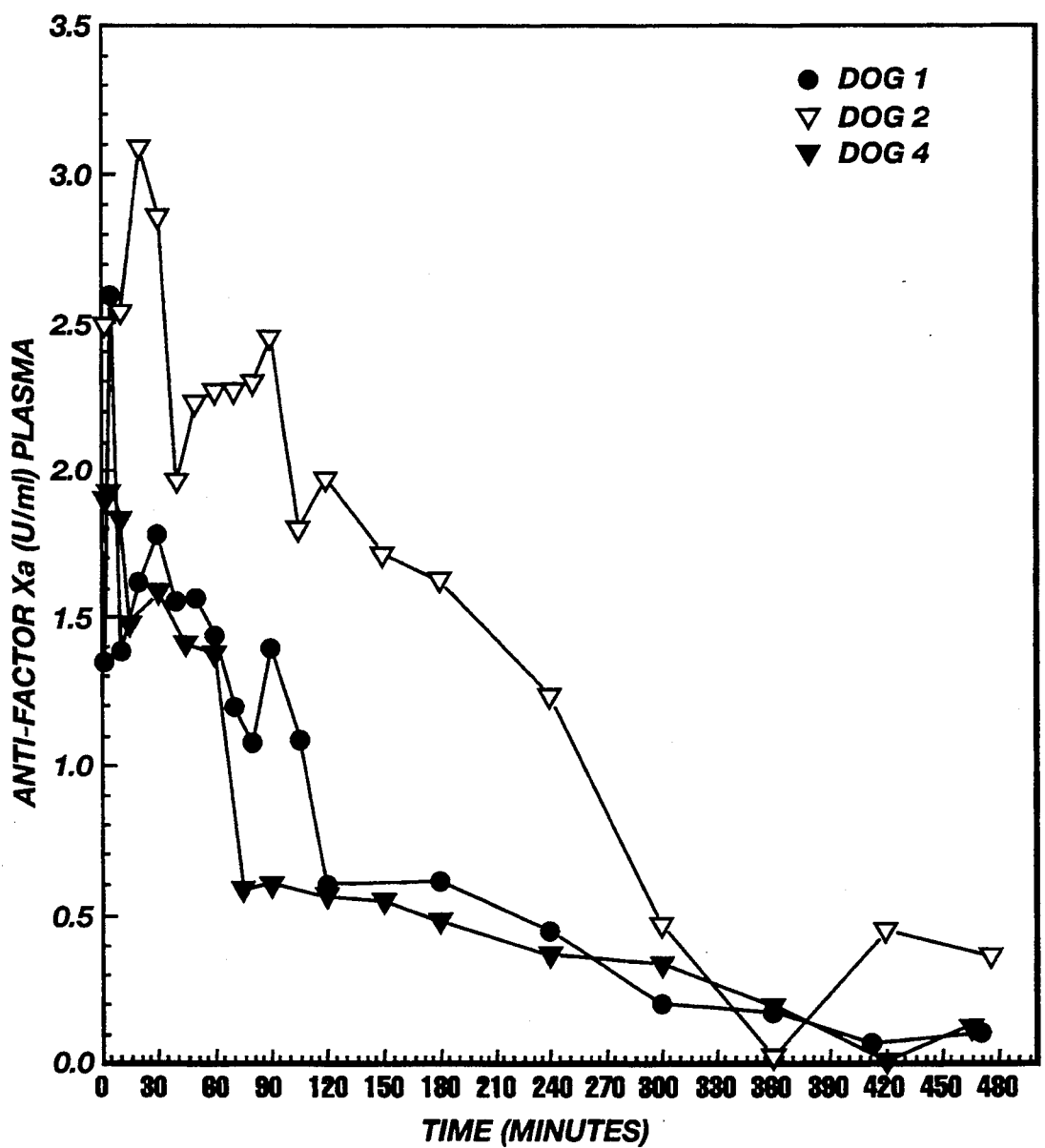
FIG. 3 shows typical heparin blood level curves for three dogs obtained after intravenous bolus administration of 5000 IU/2 ml of heparin.

The pharmacokinetic parameters for each animal were determined individually by bolus intravenous injection of 1250–5000 IU of Fragmin Heparin (10,000 IU/4 ml ampoule, Kabi, Kabivascular Service). Intravenous bolus administration of 5000 IU/2 ml resulted in the typical blood level curves shown in FIG. 3. The 5000 IU dose was chosen because it is the same as a human dose. Pharmacokinetic parameters were calculated using the two compartment model and found to exhibit typical inter-animal variability. Parameters for Dogs 1, 2, 4, 6, and 7 are presented in Table 1 which follows:

TABLE 1

Pharmacokinetic Parameters Calculated from 5000 IU Intravenous Bolus Dosing

| Dog | $AUC_{0\to\infty}$ (IU · min/ml) | $V_d$ (ml) | $K_{el}$ (min$^{-1}$) | $\alpha$ (min$^{-1}$) | $\beta$ (min$^{-1}$) |
|---|---|---|---|---|---|
| 1 | 275 | 1957 | 0.009 | 0.015 | 0.006 |
| 2 | 643 | 1563 | 0.006 | 0.003 | 0.003 |
| 4 | 268 | 2503 | 0.007 | 0.015 | 0.003 |
| 6 | 248 | 2146 | 0.010 | 0.115 | 0.006 |
| 7 | 378 | 2174 | 0.006 | 0.013 | 0.003 |
| Average | 362 | 2069 | 0.008 | 0.032 | 0.0042 |
| Standard Deviation | ±165 | ±344 | ±0.002 | ±0.047 | ±0.0016 |

Buccal Solution Cells

Control experiments were conducted to be able to compare the buccal devices with delivery of heparin by contact of heparin solutions with the buccal mucosa. Heparin solutions were prepared by dissolving dry LMWH and enhancer in deionized water. After 30 minutes of baseline sampling, 2 ml of drug solution was instilled into a 5 cm$^2$ glass cell attached to the buccal mucosa by a layer of silicone to prevent leaking. Serum samples were collected from the indwelling catheter at various times over a period of 8 hours. After 90 minutes, the drug solution was aspirated from the cell and the cell was removed. The area was wiped clean and washed free of surface drug with water. The condition of the mucosa was assessed for visible signs of tissue irritation after cell removal and at the end of the experiment.

Figure 4:
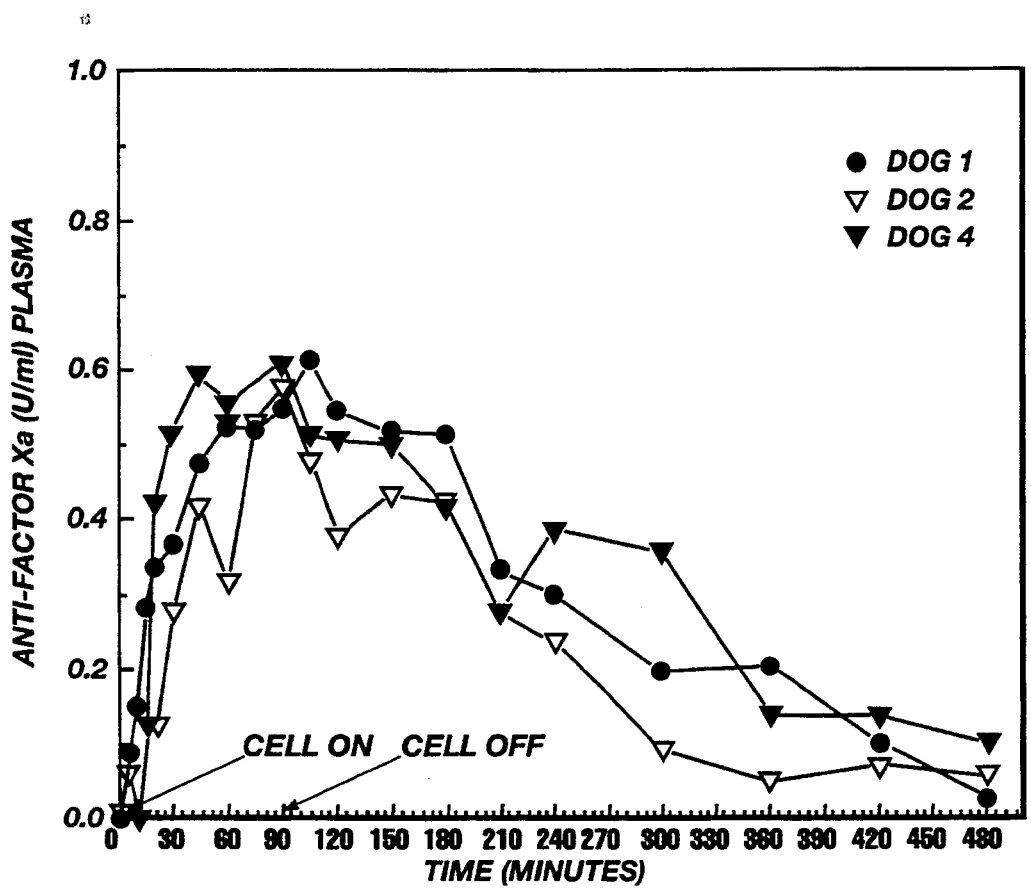
FIG. 4 shows typical heparin blood level curves for the same three dogs used in FIG. 3 obtained after administration of heparin with buccal solution cells.
Figure 5:
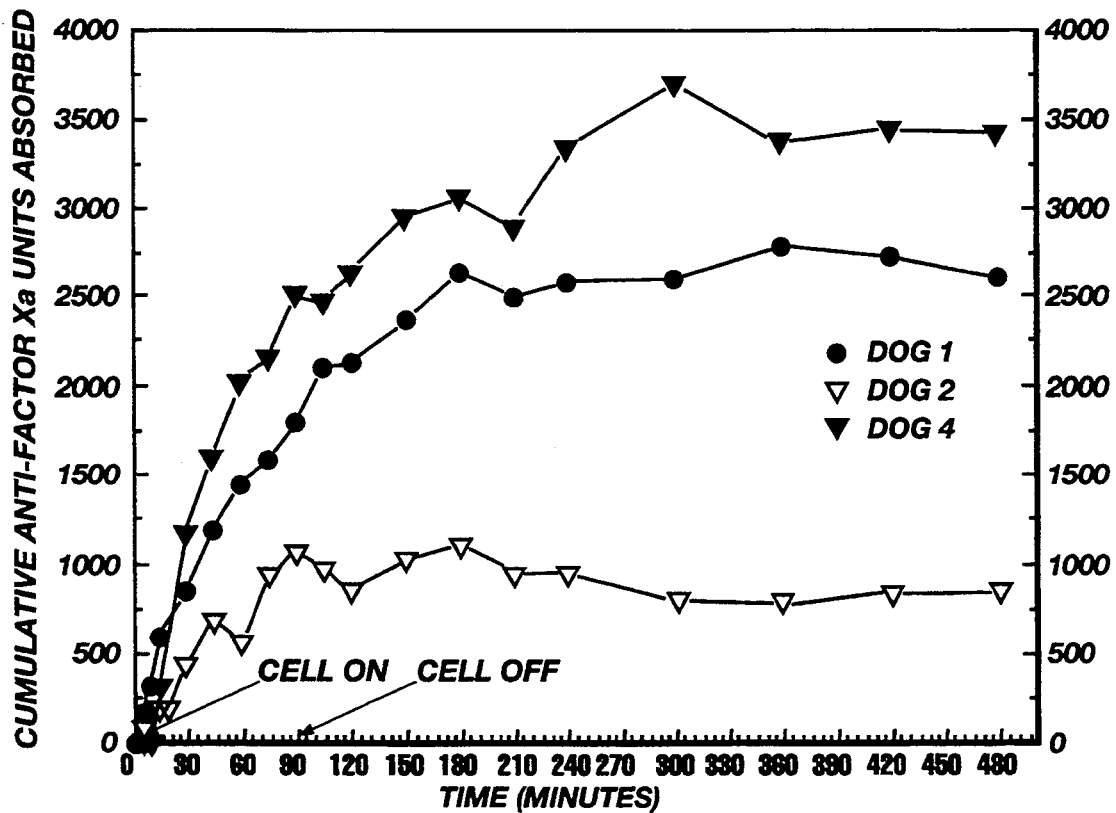
FIG. 5 complements FIG. 4 and shows cumulative amounts of heparin absorbed in the dogs after administration of heparin with buccal solution cells.

The feasibility of transmucosal heparin administration was first studied from heparin solutions. Results from buccal solution cell experiments are shown in blood level curves of FIG. 4. Although the three curves are very similar in terms of blood levels achieved, calculation of maximum amounts absorbed, based on pharmacokinetic parameters derived from intravenous bolus experiments, varied three-fold from 1070 to 3467 IU for these single experiments as shown in FIG. 5. After an initial lag time of about 5–10 minutes, drug was absorbed at a fairly constant rate during the 90 minutes in which the diffusion cell was applied. The remaining drug apparently absorbed after removal of the diffusion cell presumably represents drug binding within the mucosal tissue (i.e., depot effect) which was subsequently systemically absorbed. Pharmacokinetic parameters and constants for the buccal solution experiments are presented in Table 2.

TABLE 2

Pharmacokinetic Data for Buccal Solution Experiments

| Dog | AUC buc/iv | $V_d$ (ml) | $K_{ab}$ (min$^{-1}$) | $K_{el}$ (min$^{-1}$) | $\alpha$ (min$^{-1}$) | $\beta$ (min$^{-1}$) | Amount Absorbed |
|---|---|---|---|---|---|---|---|
| 1 | 148/275 | 1957 | 0.015 | 0.009 | 0.015 | 0.006 | 2664 IU |
| 2 | 114/643 | 1563 | 0.025 | 0.006 | 0.003 | 0.003 | 1070 IU |
| 4 | 182/268 | 2503 | 0.017 | 0.007 | 0.015 | 0.003 | 3467 IU |
| | | | | | | Average | 2400 IU |
| | | | | | | Standard Deviation | ±1220 IU |

Bucally Administered Bilayer Tablets

Figure 6:
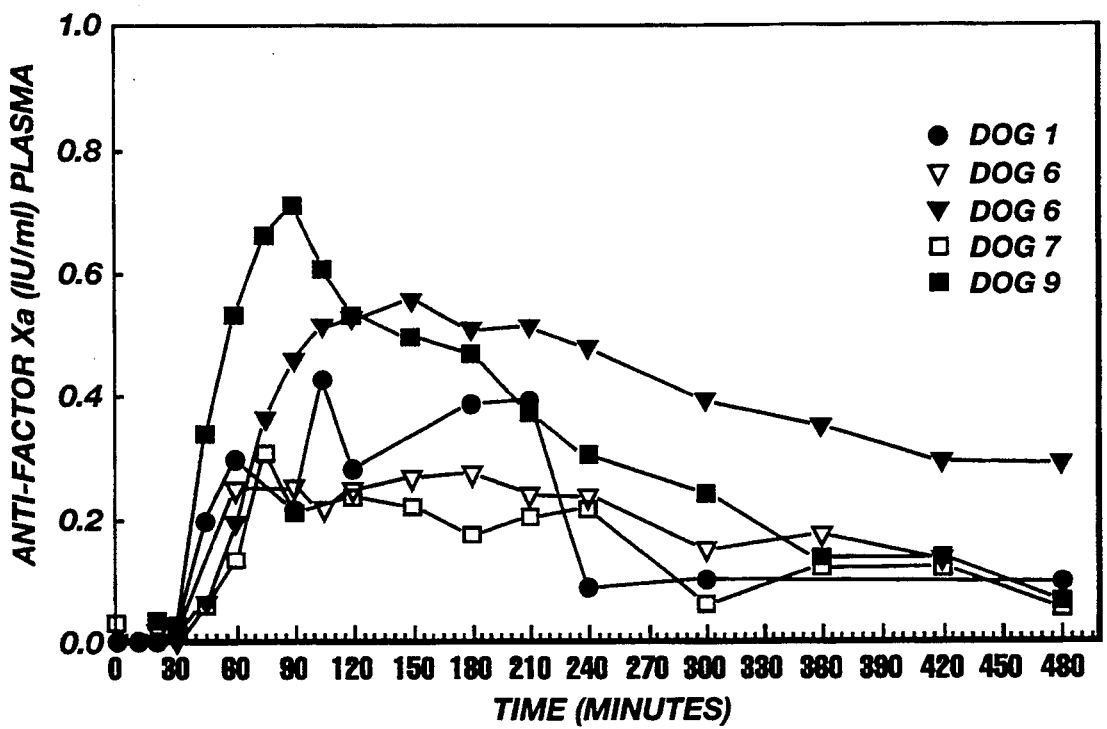
FIG. 6 shows five heparin blood level curves obtained from four dogs after administration of heparin with bilayer tablets formulated according to Example 1.
Figure 7:
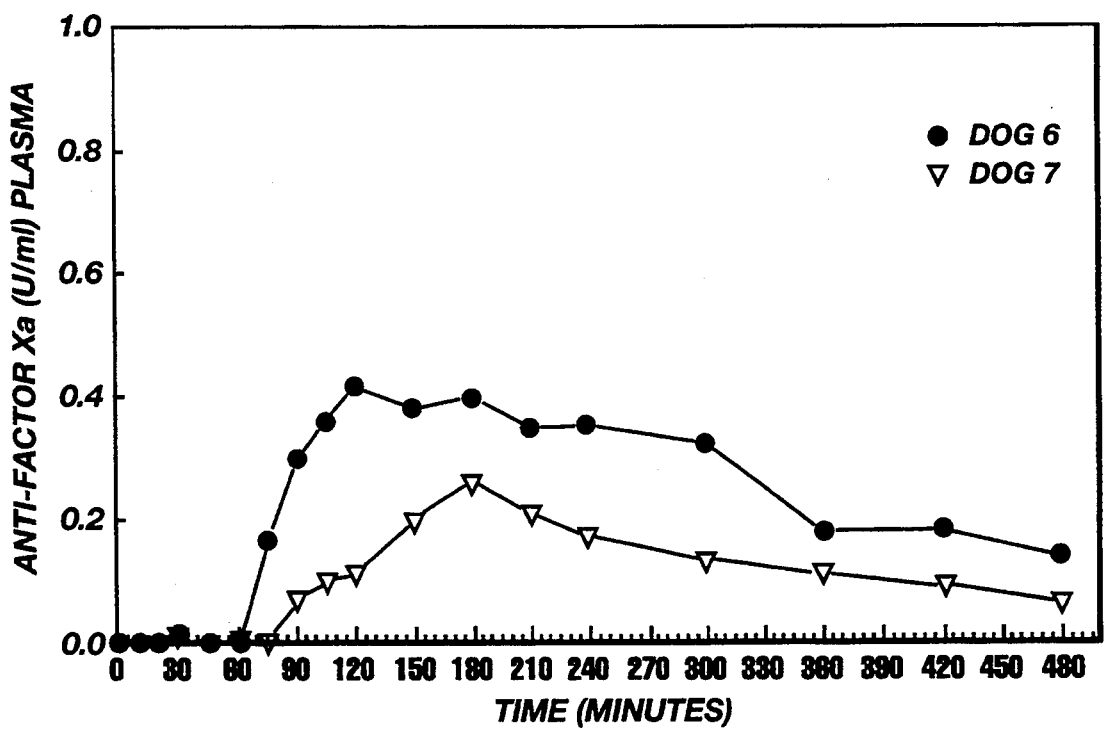
FIG. 7 shows heparin blood level curves obtained from two dogs after administration of heparin with bilayer tablets formulated according to Example 2.
Figure 8:
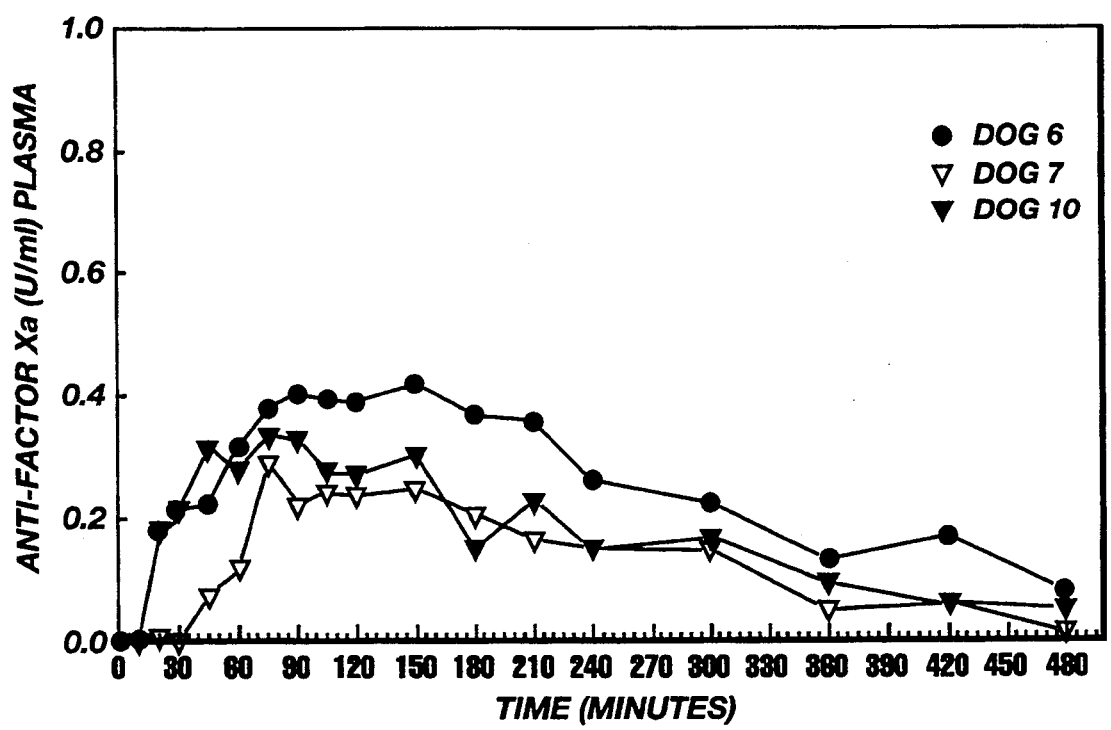
FIG. 8 shows heparin blood level curves obtained from three dogs after administration of heparin with bilayer tablets formulated according to Example 3.
Figure 9A:
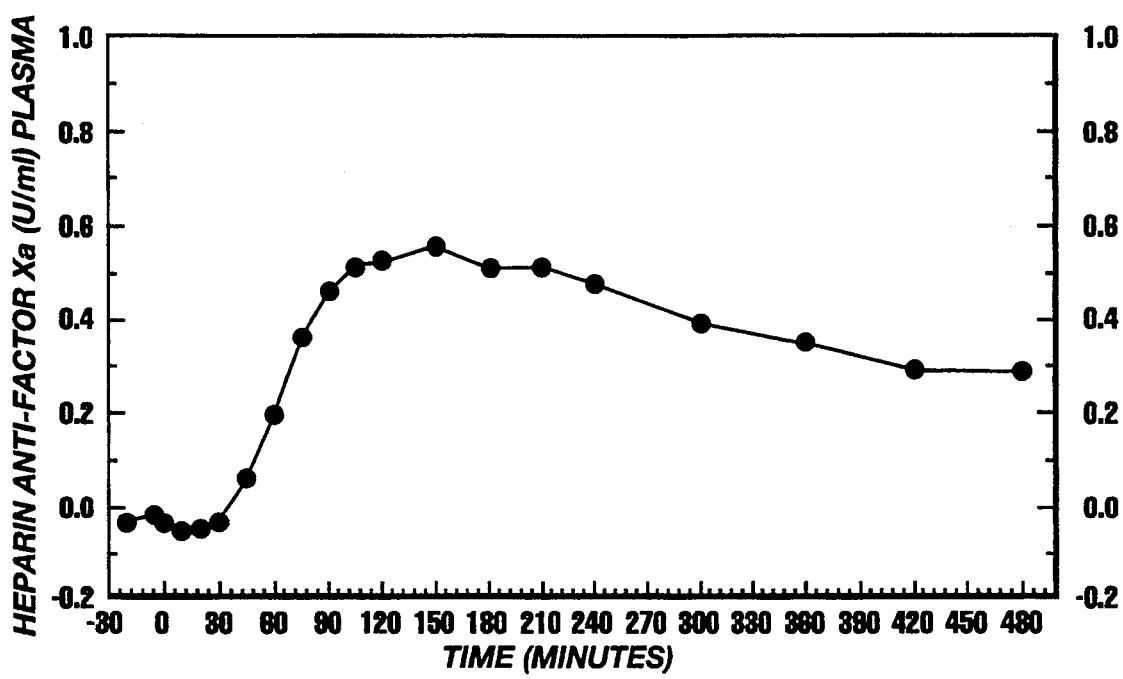
FIG. 9a shows the heparin blood level curve from one dog in FIG. 6
Figure 9B:
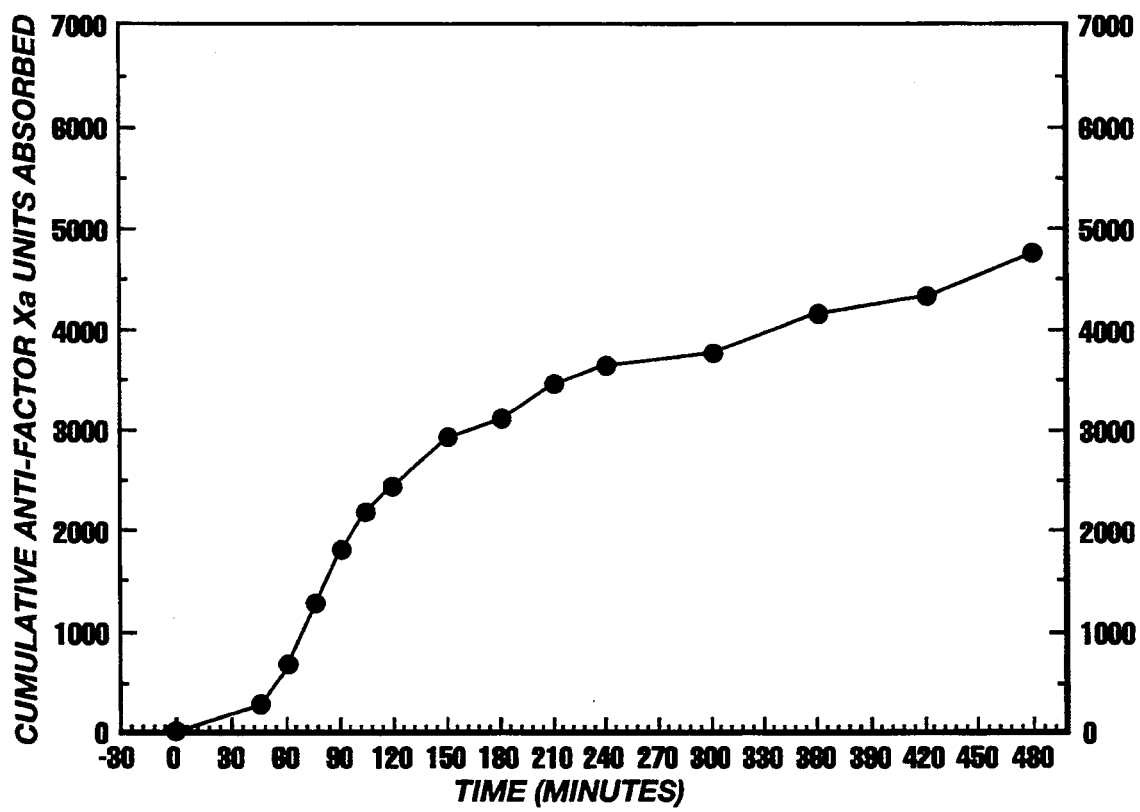
FIG. 9b shows the cumulative amount of heparin absorbed in that dog following administration of heparin with bilayer tablets formulated in accordance with Example 1.

Experiments involving the buccal dosage forms also involved drawing and pooling 30 minutes of baseline samples prior to starting the experiment. At the commencement of the experiment, tablets or patches were applied to the buccal mucosa. With the dog lying on its side, a fairly large buccal area was presented. Tablets were arranged in a triangle with the active layer contacting the mucosa and the inert layer facing upward. To prevent dehydration of the mucosa with the anesthetized dogs, irrigation was begun immediately with 200 μl of saline solution applied in the center of the triangle formed by the tablets. Every hair hour for the first 4 hours and hourly thereafter, 100 μl of saline solution was similarly applied. The inert layer slowly disintegrated during the course of the experiment while the active layer typically dissolved within an hour. Transmucosal transport of LMWH from the bilayer tablets of Examples 1, 2 and 3, respectively, resulted in anti-factor $X_a$ blood levels in the 0.2–0.5 IU/ml plasma range for these three different tablet formulations as shown in FIGS. 6–8. FIG. 6 shows five heparin blood level curves using dogs 1, 6, 7 and 9 obtained after administration of heparin with bilayer tablets formulated according to Example 1. FIG. 7 shows heparin blood level course obtained from two dogs after administration of heparin with bilayer tablets formulated according to Example 2. FIG. 8 shows heparin blood levels curves obtained from three dogs after administration of heparin with bilayer tablets formulated according to Example 3. FIG. 9a shows again the heparin blood level curve for Dog 6, from FIG. 6, and FIG. 9b shows the deconvoluted LMWH absorption profile FIG. 9b shows almost 4800 IU of heparin was absorbed cumulatively. Tables 3, 4 and 5 detail results of pharmacokinetic calculations and show that the tablets of Example 1, 2 and 3 deliver significant levels of heparin.

TABLE 3

Pharmacokinetic Data for Buccal Tablet Experiments
(Buccal Tablets Formed In Example 1)

| Dog | AUC buc/iv | $V_d$ (ml) | $K_{ab}$ (min$^{-1}$) | $K_{el}$ (min$^{-1}$) | $\alpha$ (min$^{-1}$) | $\beta$ (min$^{-1}$) | Amount Absorbed |
|---|---|---|---|---|---|---|---|
| 1 | 103/275 | 1957 | 0.013 | 0.009 | 0.015 | 0.006 | 1881 IU |
| 6 | 102/248 | 2146 | 0.008 | 0.010 | 0.115 | 0.006 | 2145 IU |
| 6 | 226/248 | 2146 | 0.006 | 0.010 | 0.115 | 0.006 | 4392 IU |
| 7 | 83/378 | 2174 | 0.013 | 0.006 | 0.013 | 0.003 | 1053 IU |
| | | | | | | Average | 2368 IU |
| | | | | | | Standard Deviation | ±1427 IU |

TABLE 4

Pharmacokinetic Data for Buccal Tablet Experiments
(Buccal Tablets Formed In Example 2)

| Dog | AUC buc/iv | $V_d$ (ml) | $K_{ab}$ (min$^{-1}$) | $K_{el}$ (min$^{-1}$) | $\alpha$ (min$^{-1}$) | $\beta$ (min$^{-1}$) | Amount Absorbed |
|---|---|---|---|---|---|---|---|
| 6 | 138/248 | 2146 | 0.008 | 0.010 | 0.115 | 0.006 | 2875 IU |
| 7 | 73/378 | 2174 | 0.008 | 0.006 | 0.013 | 0.003 | 890 IU |
| | | | | | | Average | 1883 IU |
| | | | | | | Standard Deviation | ±1404 IU |

TABLE 5

Pharmacokinetic Data for Buccal Tablet Experiments
(Buccal Tablets Formed In Example 3)

| Dog | AUC buc/iv | $V_d$ (ml) | $K_{ab}$ (min$^{-1}$) | $K_{el}$ (min$^{-1}$) | $\alpha$ (min$^{-1}$) | $\beta$ (min$^{-1}$) | Amount Absorbed |
|---|---|---|---|---|---|---|---|
| 6 | 134/248 | 2146 | 0.008 | 0.010 | 0.115 | 0.006 | 2746 IU |
| 7 | 65/378 | 2174 | 0.031 | 0.006 | 0.013 | 0.003 | 966 IU |
| | | | | | | Average | 1856 IU |
| | | | | | | Standard Deviation | ±1259 IU |

As shown in Tables 4 and 5, experiments with lower levels of heparin (Table 5, Example 3), or with a different enhancer, (Table 4, Example 2) respectively, also resulted in significant levels of LMWH absorption.

Similar types of results regarding levels of calcitonin absorption are found when using bilayer tablets formulated according to Examples 4 and 5.

Figure 13A:
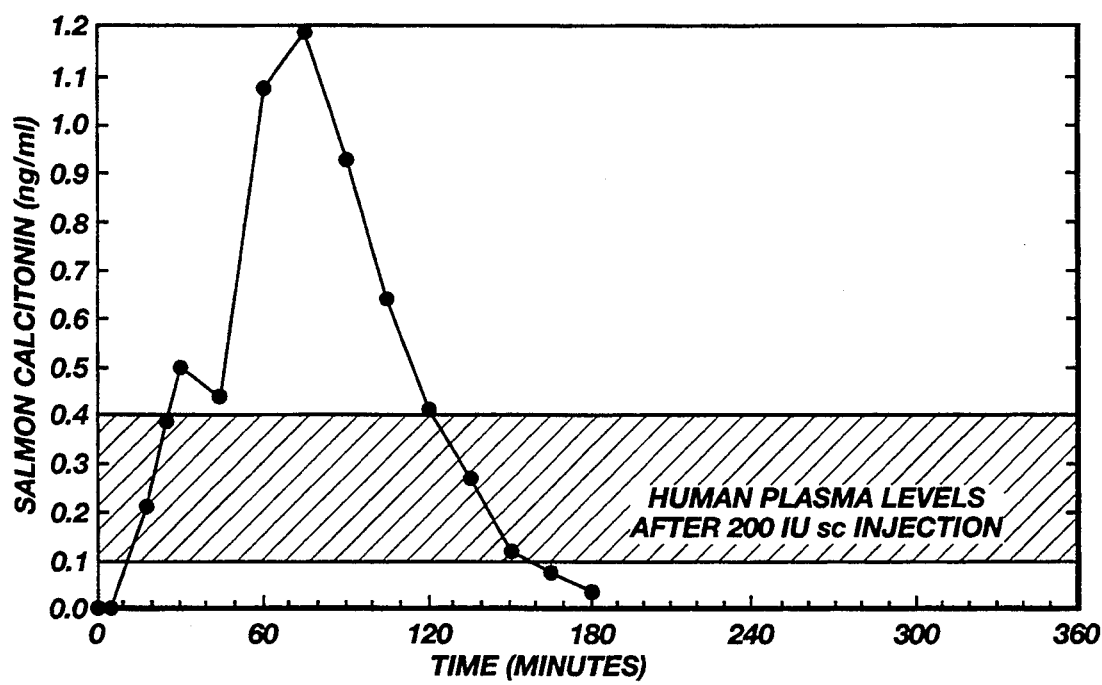
FIG. 13a shows the salmon calcitonin blood level curve obtained from dogs after administration of 1 mg calcitonin with buccal solution cells and FIG. 13b shows the cumulative amount of calcitonin absorbed in that dog following administration of calcitonin with buccal solution cells.
Figure 13B:
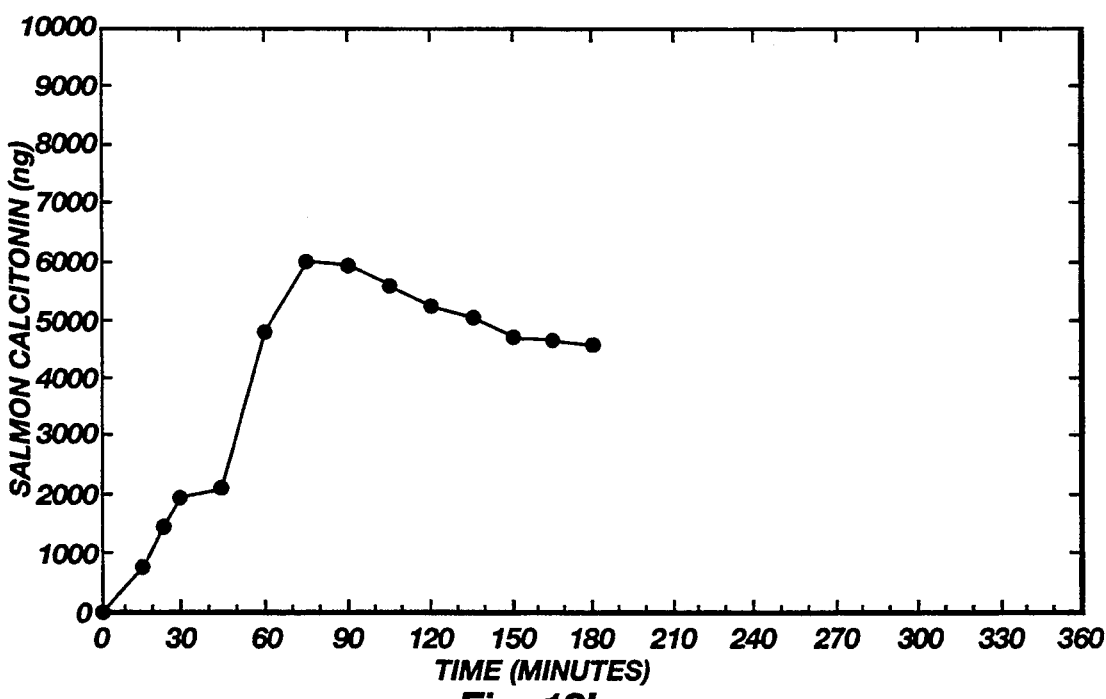

Buccal transport was initially verified from calcitonin solution experiments using buccal cells as described above for heparin. For purposes of comparison, therapeutic human plasma levels after 200 IU salmon calcitonin injection are generally between 0.1 and 0.4 ng/ml. As shown in FIG. 13a, plasma level profiles of 0.1 ng/ml salmon calcitonin (SCT) blood levels were obtained within 15 minutes and then proceeded to rise to 1.2 ng/ml, which is well above 0.4 ng/ml level, at 90 minutes. FIG. 13b shows the calculated absorption plot for the same experiment. A total of 30 IU (0.006 mg) was absorbed.

Figure 14A:
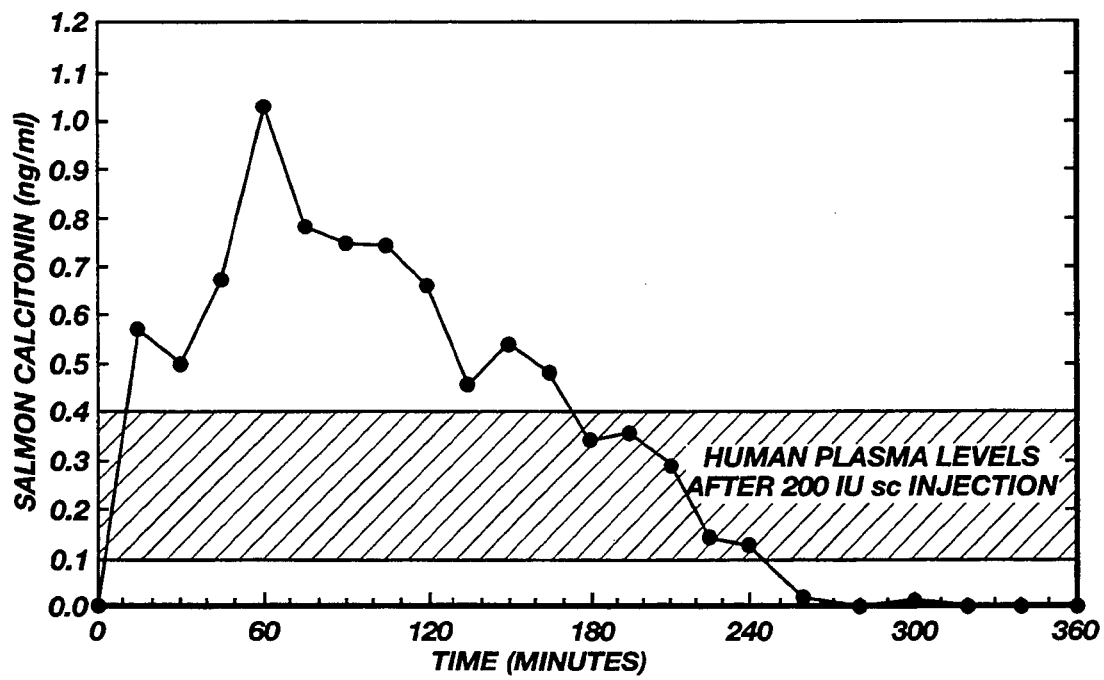
FIG. 14a shows the salmon calcitonin blood level curve obtained from the same dogs used in FIG. 13
Figure 14B:
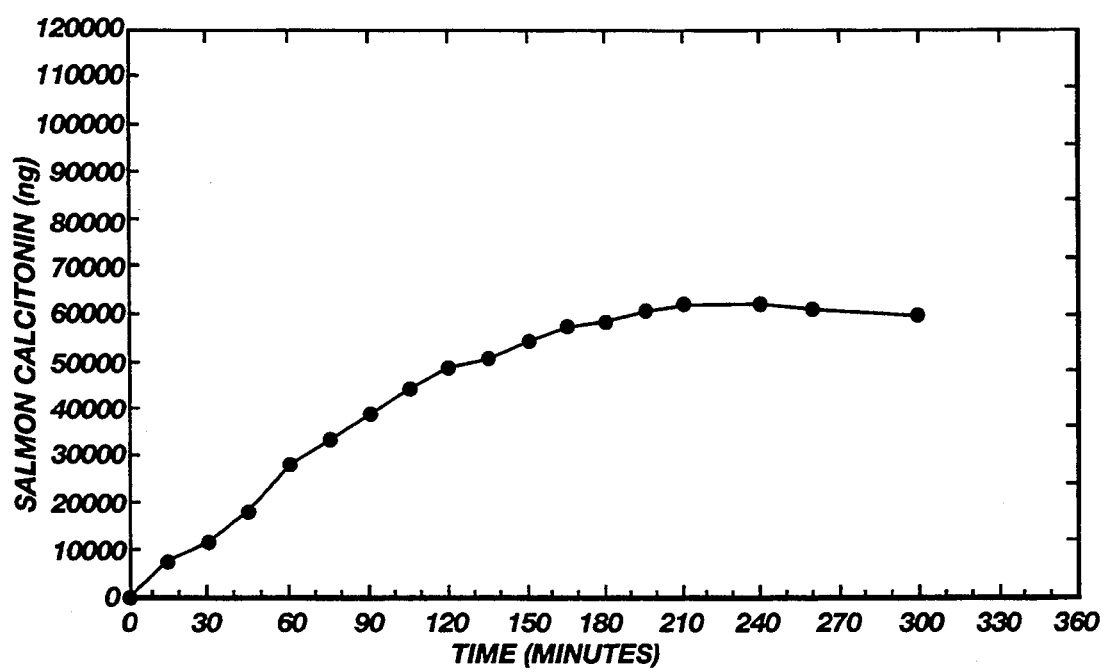
FIG. 14b shows the cumulative amount of calcitonin absorbed following administration of 1 mg of salmon calcitonin formulated in bilayer tablets in accordance with the dry blend procedure of Example 4.
Figure 15A:
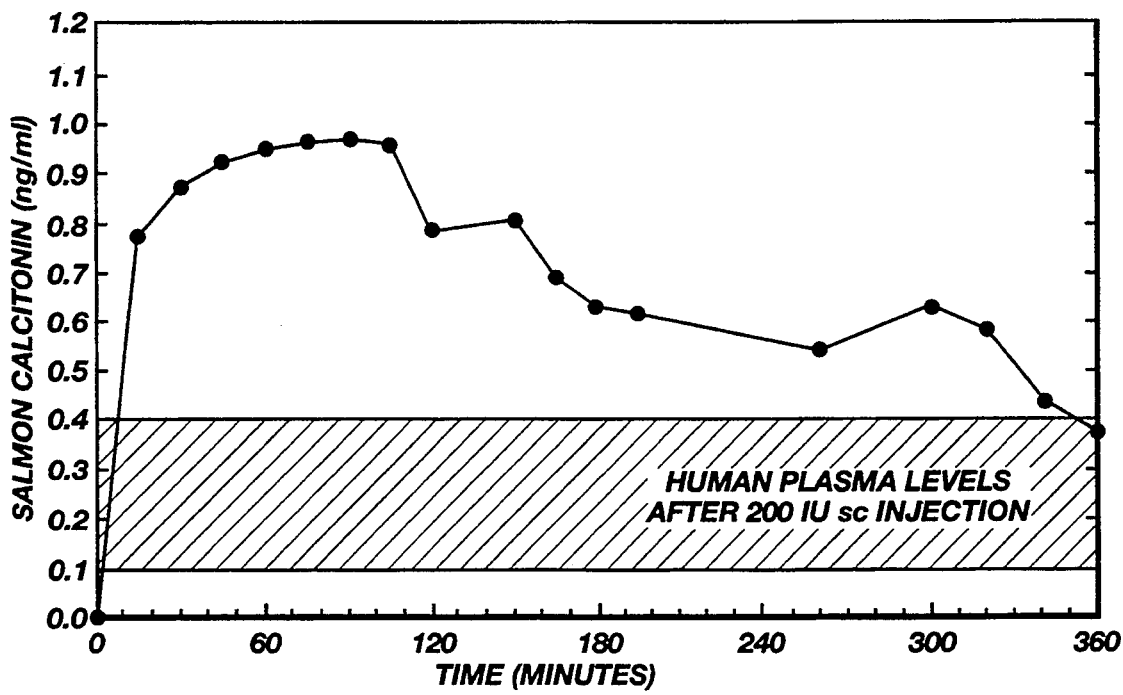
FIG. 15a shows the salmon calcitonin blood level curve obtained from the same dogs used in FIGS. 13 and 14 and FIG. 15b shows the cumulative amount of calcitonin absorbed following administration of 1 mg of salmon calcitonin formulated in bilayer tablets in accordance with the wet granulation procedure of Example 5.
Figure 15B:
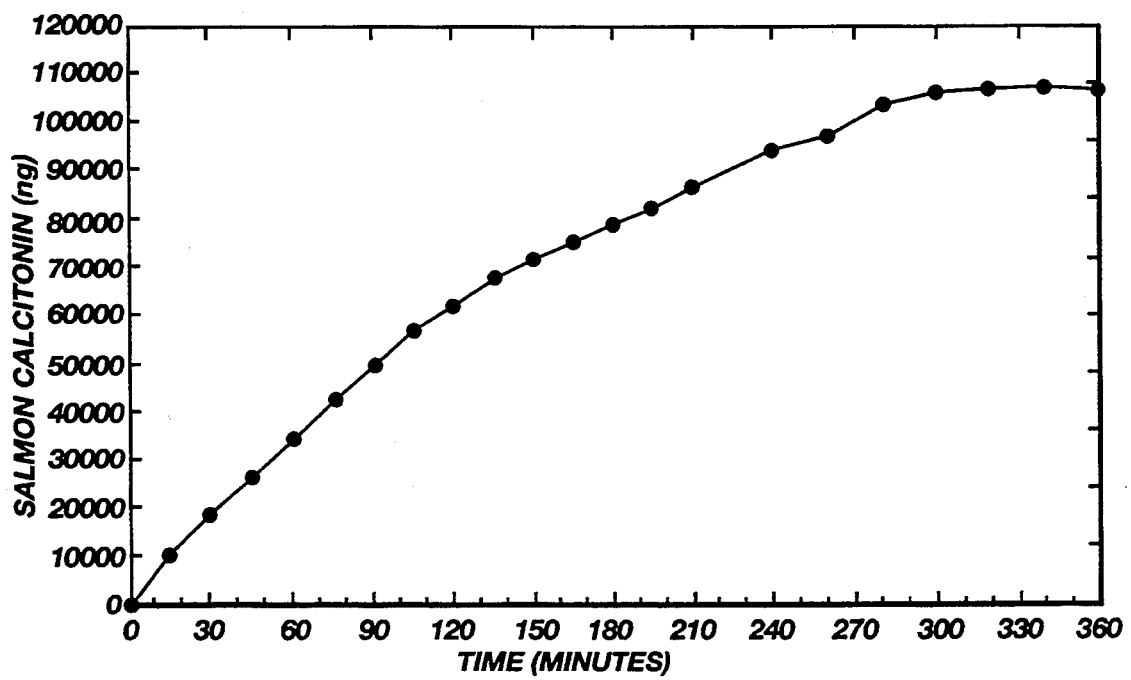

When using the transbuccal calcitonin tablets formulated in Example 4 and 5 which were applied and monitored in dogs in the same manner as the heparin experiments outlined above, the plasma level profiles of calcitonin showed almost no lag times and were comparable to the buccal solution cell experiment. FIG. 14a shows the plasma level curve following buccal application of the dry compression bilayer tablets of Example 4 and FIG. 14b shows the calculated absorption profile for these tablets. A total of 249 IU (0.0623 mg) of SCT was continuously delivered during the six hour experiment. Similarly, FIG. 15a shows the plasma level curve following buccal application of wet granulated transbuccal tablets prepared in Example 5 and FIG. 15b shows the calculated absorption profile for these tablets. A total of 550 IU (0.11 mg) of SCT was continuously delivered during the six hour experiment.

From a comparison of FIGS. 13, 14 and 15 it is apparent that the buccal tablets provide a longer duration of action than the buccal solution does. In FIG. 13 it can be see that the SCT in the blood starts to drop before the solution cells were removed at 90 minutes. Moreover, the tablets clearly provided much higher total SCT absorption.

Buccally Administered Filmpatch Devices

Filmpatches prepared in Example 6 were applied to the buccal mucosa with the active side down and the perm-selective membrane facing the oral cavity. The filmpatch was irrigated on the same schedule as in the tablet experiments. The active layer dissolved and became transparent within 30 minutes. Insoluble perm-selective membranes were removed at 5-6 hours.

Figure 10A:
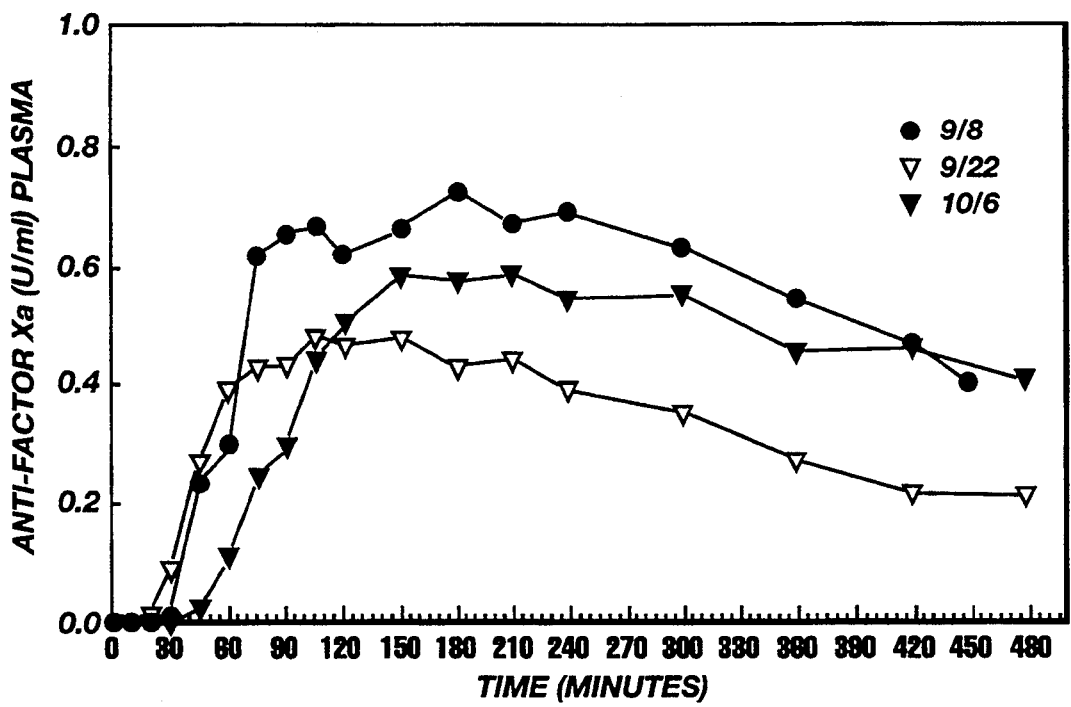
FIG. 10a shows the heparin blood level curves from three different test dates using the same dog and FIG. 10b shows the cumulative amount of heparin absorbed after administration of heparin with filmpatches made in accordance with Example 6.
Figure 10B:
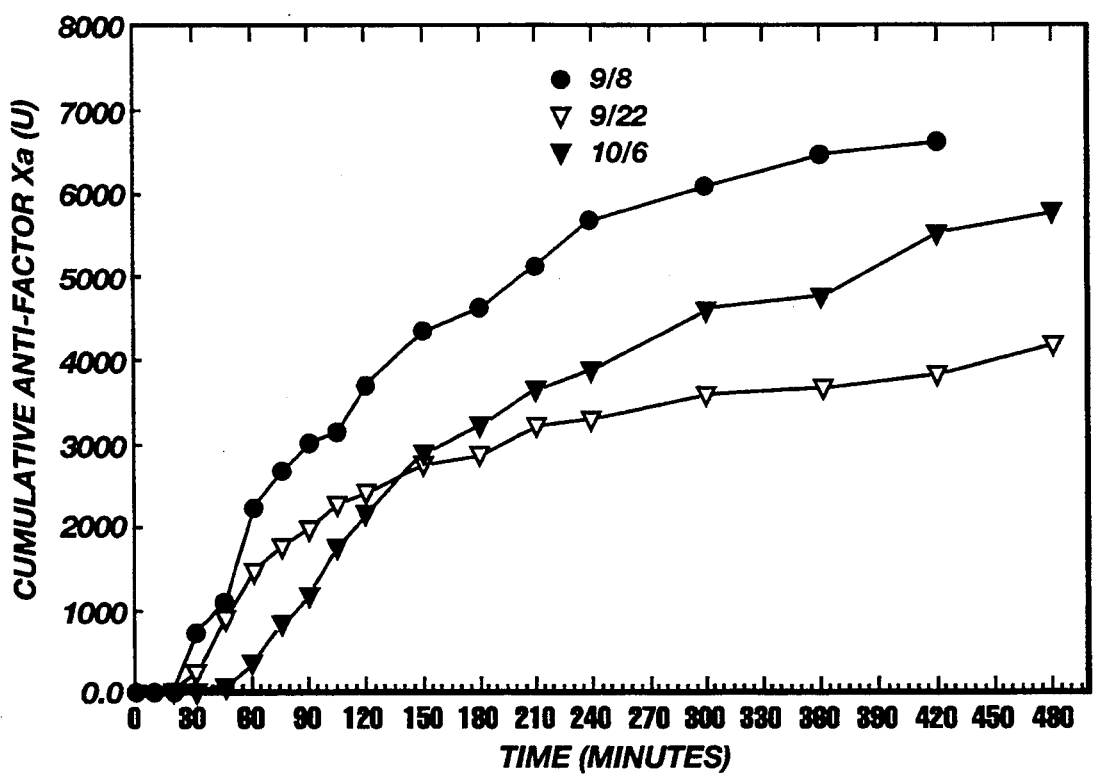
Figure 11:
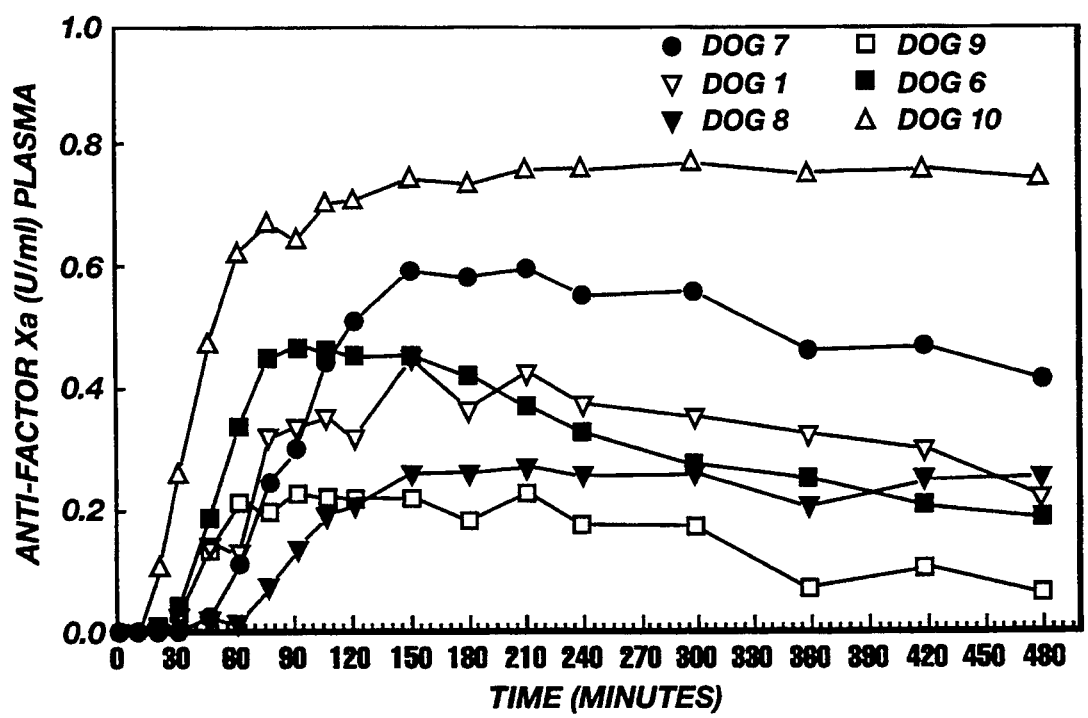
FIG. 11 shows heparin blood level curves obtained from six dogs after administration of heparin with filmpatches made in accordance with Example 6.
Figure 12A:
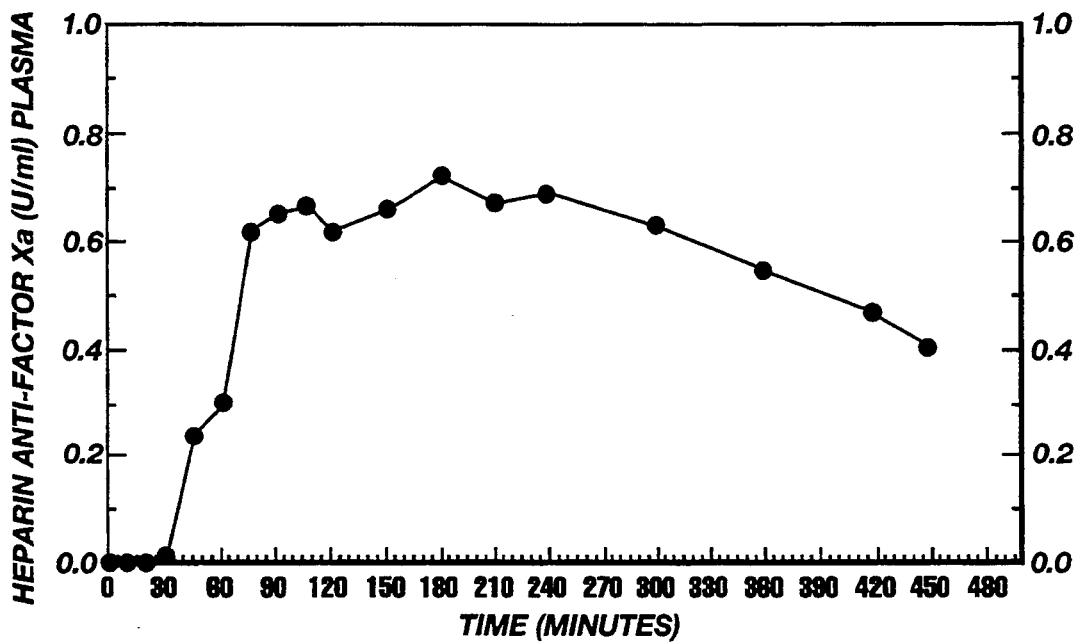
FIG. 12a shows, in isolation, the highest level heparin blood level curve from FIG. 10a and FIG. 12b shows the cumulative amount of heparin absorbed from that test following administration of heparin with filmpatches formulated in accordance with Example 6.
Figure 12B:
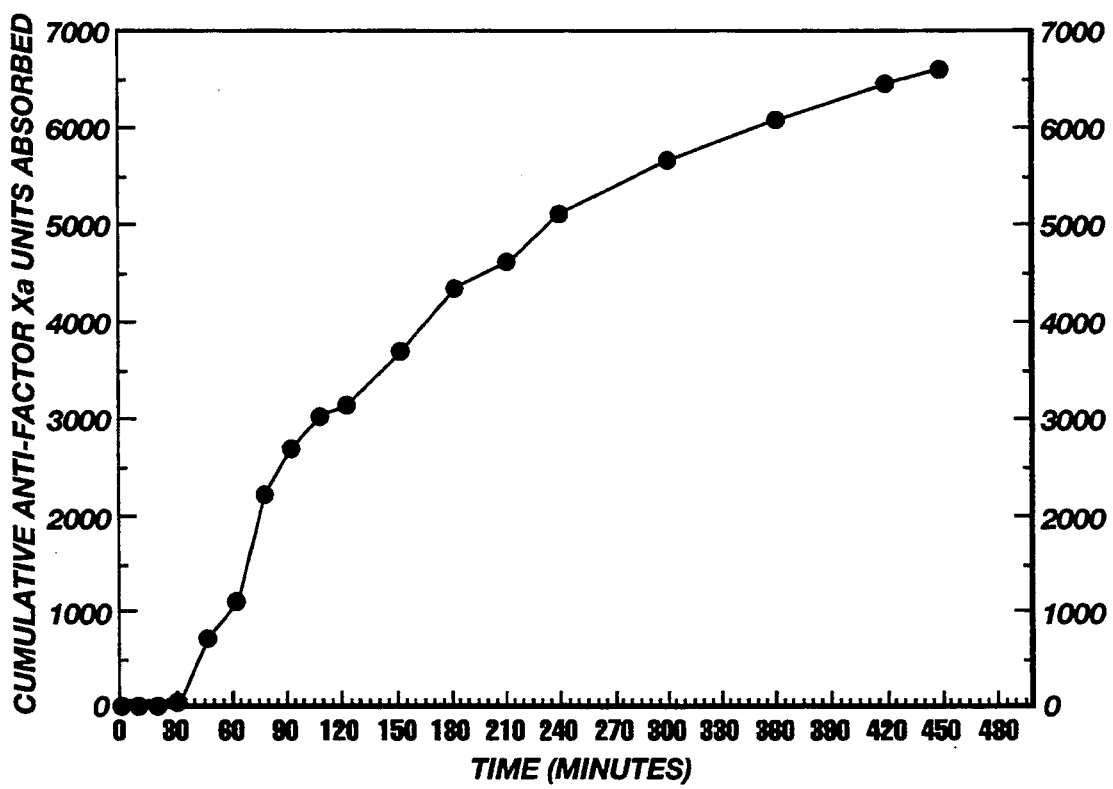

Heparin blood levels from buccal filmpatch devices turned out to be approximately 50% higher than from bilayer tablets, ranging from 0.3-0.7 IU/ml of plasma as shown in FIGS. 10a and 12a. As shown in FIG. 12b more than 6500 IU or 40.4 mg was cumulatively absorbed according to the deconvoluted heparin absorption profile during the course of an 8 hour period. Furthermore, FIG. 12a shows that blood levels are still not back to baseline at 8 hours, possibly indicating a significant tissue depot effect. FIG. 11 shows a somewhat greater variation in blood level curves from that shown in FIG. 10a but, with one exception, still shows sustained heparin levels in the range of between about 0.2-0.75 IU/ml of plasma. These results are consisting with those reported in Table 6 which shows a variation of from about 2230 to about 6500 IU LMWH cumulatively absorbed from the Filmpatch of Example 6.

TABLE 6

Pharmacokinetic Data for Buccal Filmpatch Experiments
(Filmpatch Formed In Example 6)

| Dog | AUC buc/iv | $V_d$ (ml) | $K_{ab}$ (min$^{-1}$) | $K_{el}$ (min$^{-1}$) | $\alpha$ (min$^{-1}$) | $\beta$ (min$^{-1}$) | Amount Absorbed |
|---|---|---|---|---|---|---|---|
| 1 | 137/275 | 1957 | 0.005 | 0.009 | 0.015 | 0.006 | 2229 IU |
| 6 | 314/248 | 2146 | 0.005 | 0.010 | 0.115 | 0.006 | 6504 IU |
| 6 | 195/248 | 2166 | 0.005 | 0.010 | 0.115 | 0.006 | 4108 IU |
| 6 | 277/248 | 2146 | 0.006 | 0.010 | 0.115 | 0.006 | 5736 IU |
| 7 | 215/378 | 2174 | 0.005 | 0.006 | 0.013 | 0.003 | 2549 IU |
| | | | | | | Average | 4225 IU |
| | | | | | | Standard Deviation | ±1890 IU |

Absorption from these devices appears to be increased by the use of a perm-selective backing material. In these devices, the perm-selective membrane was a 500 molecular weight cutoff dialysis membrane that allowed water and other small molecules to penetrate and dissolve the active layer. At the same time, larger molecules like LMWH and other components were prevented from diffusing into the buccal cavity and held in close contact with the mucosa. Also active ingredients were less prone to uncontrolled dilution and dissipation from the transport site.

During the course of these buccal transport experiments, the condition of the buccal mucosa was routinely monitored as noted above for the solution experiments. No outward signs of irritation were noted and no changes in the appearance or texture were detected by visual observation or tactile palpation even though individual animals were used repeatedly for several months.

Although these experiments domonstrate the buccal delivery of LMWH from both bilayer tablets and film patches, the same techniques can be utilized to deliver other macromolecules having a molecular weight of about 500 daltons or above. Generally, drugs having a molecular weight of between about 500 to 10,000 daltons are can be effectively delivered. However, drugs ranging between about 500 and 6000 daltons are preferred. As noted above, the invention is particularly adapted to the delivery of polysaccharides, polypeptides and proteins. Most particularly, the invention facilitates the delivery of charged molecules which are generally most difficult to administer through the oral mucosa.

Therefore, the above examples are but illustrative of drugs or transmucosal formulations which may be employed in operation of the present invention. The invention is directed to the discovery that the proper formulation of macromolecular drugs, bile salt enhancers and hydrophilic polymers provides for the transmucosal delivery of macromolecules to the oral mucosa. While LMWH as a drug, NaTC and CHAPS as bile salt enhancers and hydroxypropyl cellulose as the hydrophilic polymer have been primarily used for purposes of illustration other drugs, bile salt enhancers and hydrophilic polymers may also be utilized and similar results will be realized. Therefore, within the guidelines presented herein, a certain amount of experimentation to obtain optimal formulations can be readily carried out by those skilled in the art. Therefore, the invention is limited in scope only by the following claims and functional equivalents thereof.

We claim:

1. A system for mucosally administering a macromolecular drug to the oral cavity comprising an inner drug/enhancer/polymer layer having one surface adapted to contact the mucosal tissue of the oral cavity and adhere thereto when wet and an opposing surface in contact with and adhering to an overlying inert layer, said inner layer containing from about two to sixty percent by weight of a bile salt enhancer, five to sixty five percent by weight of a hydrophilic polymer and an effective amount of a macromolecular drug having a molecular weight of at least 500 daltons.

2. A system according to claim 1 wherein said bile salt enhancer is a steroidal detergent comprising the natural or synthetic salts of cholanic acid and mixtures thereof.

3. A system according to claim 2 wherein said macromolecular drug is a member selected from the group consisting of polysaccharides, polypeptides and proteins.

4. A system according to claim 3 wherein said hydrophilic polymer is a member selected from the group consisting of hydroxypropyl cellulose, hydroxypropyl methylcellulose, hydroxy ethylcellulose, ethylcellulose, carboxymethyl cellulose, dextran, gaur-gum, polyvinyl pyrrolidone, pectins, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, and mixtures thereof.

5. A system according to claim 4 in the form of a bilayer tablet wherein said inner layer additionally contains one or more members selected from the group consisting of binding agents, flavoring agents and fillers and wherein said inert layer is nonadhesive to mucosal tissues and is substantially impermeable to the bile salt enhancer or macromolecular drug.

6. A system according to claim 5 wherein said bile salt enhancer is a salt of a conjugate of a bile acid with taurine.

7. A system according to claim 6 wherein said hydrophilic polymer is hydroxypropyl cellulose.

8. A system according to claim 7 wherein the macromolecular drug is a polysaccharide.

9. a system according to claim 8 wherein the polysaccharide is heparin having a molecular weight of between about 4000 and 6000.

10. A system according to claim 7 wherein the macromolecular drug is a polypeptide.

11. A system according to claim 10 wherein the polypeptide is calcitonin.

12. A system according to claim 4 in the form of a filmpatch wherein said inert layer is a polymeric membrane which is nonadhesive to mucosal tissues and is substantially impermeable to the bile salt enhancer or macromolecular drug.

13. A system according to claim 12 wherein said membrane is a perm-selective membrane having a desired molecular weight cutoff pore structure.

14. A system according to claim 13 wherein said membrane has a molecular weight cutoff of between about 100 and 500.

15. A system according to claim 14 wherein said bile salt enhancer is a salt of a conjugate of a bile acid with taurine.

16. A system according to claim 15 wherein said hydrophilic polymer is hydroxypropyl cellulose.

17. A system according to claim 16 wherein the macromolecular drug is a polysaccharide.

18. A system according to claim 17 wherein the polysaccharide is heparin having a molecular weight of between about 4000 and 6000.

19. A system according to claim 16 wherein the macromolecular drug is a polypeptide.

20. A system according to claim 19 wherein the polypeptide is calcitonin.

21. A system according to claim 13 wherein an additional membrane overlays and extends beyond the periphery of said molecular weight cutoff membrane and contains an adhesive on the portion of the inner surface thereof extending beyond said inert layer for adhering said system to mucosal tissues.

22. A system according to claim 21 wherein said additional membrane is also a perm-selective membrane having a desired molecular weight cutoff pore structure.

23. A system according to claim 22 wherein the molecular weight cutoff of said inert membrane is between about 100 and 500 and wherein the molecular weight cutoff of said inert membrane and said additional membrane are different.

24. A system according to claim 23 wherein each of the inert layer and additional layer is a molecular weight cutoff membrane having a molecular weight cutoff of between 100 and 500.

* * * * *